United States Patent [19]

Berneis et al.

[11] Patent Number: 5,478,569
[45] Date of Patent: Dec. 26, 1995

[54] FAT-SOLUBLE COMPOSITION OF COLLOIDAL FISH GELATIN

[75] Inventors: Kurt Berneis, Ettingen; Peter Schuler, Basel, both of Switzerland

[73] Assignee: Hoffmann-La Roche Inc., Nutley, N.J.

[21] Appl. No.: 345,174

[22] Filed: Nov. 28, 1994

Related U.S. Application Data

[63] Continuation of Ser. No. 240,796, May 10, 1994, abandoned, which is a continuation of Ser. No. 133,819, Oct. 6, 1993, abandoned, which is a continuation of Ser. No. 830,043, Jan. 31, 1992, abandoned, which is a continuation of Ser. No. 595,728, Oct. 9, 1990, abandoned, which is a continuation of Ser. No. 367,171, Jun. 16, 1989, abandoned.

[30] Foreign Application Priority Data

Jun. 23, 1988 [CH] Switzerland ............... 2416/88
Apr. 17, 1989 [CH] Switzerland ............... 1444/89

[51] Int. Cl.⁶ ............... A61K 9/64; A61K 9/56; A61K 9/14; A61K 9/16; A61K 31/59; A61K 31/355; A61K 31/34; A61K 31/12; A61K 31/07
[52] U.S. Cl. ............... 424/456; 424/459; 424/460; 424/489; 424/490; 424/492; 514/167; 514/458; 514/474; 514/681; 514/725; 514/944; 514/851
[58] Field of Search ............... 424/456, 459, 424/460, 489, 490, 492; 514/167, 458, 681, 725, 474, 944, 951

[56] References Cited

U.S. PATENT DOCUMENTS

| | | | |
|---|---|---|---|
| 2,756,177 | 7/1956 | Cannalonga et al. | 167/81 |
| 3,655,406 | 4/1172 | Klaui | 99/148 C |
| 5,035,896 | 7/1991 | Apfel et al. | 424/456 |

OTHER PUBLICATIONS

Technical Bulletin re: Vitamin A Acetate Dry Powder 25 CWD of BASF, Jan. 1985.
Technical Bulletin re: Gelita Specizal (Gelita–Sol) of Deutsche–Gelatin–Fabriken Stoess & Co., GmbH, Sept., 1982.
Jacobsen, Kim, Microencapsulated Feed For Marine Fish Larvae, pp. 58, 59, 62, 63, 99–101, 116–117 (1987).
Technical Bulletin re: Vitamin A Acetate Dry Powder CWD of BASF, Jan. 1986.
Technical Bulletin re: Vitamin A Palmitate Dry Powder CWD of BASF, Feb., 1986.

Primary Examiner—T. J. Criares
Attorney, Agent, or Firm—George M. Gould; William H. Epstein; Catherine A. Picut

[57] ABSTRACT

Stable, cold water-dispersible, liquid or pulverous compositions of fat-soluble substances which contain fish gelatin as the protective colloid and a method of making same are described.

11 Claims, No Drawings

FAT-SOLUBLE COMPOSITION OF COLLOIDAL FISH GELATIN

This is a continuation of application Ser. No. 08/240,796 filed May 10, 1994, which is a continuation of application Ser. No. 08/133,819 filed Oct. 6, 1993, which is a continuation of Ser. No. 07/830,043 filed Jan. 31, 1992, which is a continuation of Ser. No. 07/595,728, filed Oct. 9, 1990 which is continuation of Ser. No. 07/367,171 filed Jun. 16, 1989.

FIELD OF THE INVENTION

The present invention is concerned with novel, stable, cold water-dispersible preparations of fat-soluble substances and with a process for their preparation.

BACKGROUND OF THE INVENTION

Compositions containing fat-soluble substances are useful as human and animal nutritional supplements.

In the known art such fat-soluble or active substances are enveloped in a protective colloid. The colloid generally used is gelatin originating from warm-blooded animals and such origin is often problematic.

For example, preparations based on such gelatin can not be used worldwide for religious reasons. Also without an expensive manufacturing process of this gelatin from warm blooded animals, the resulting manufactured preparations do not always have a desired dispersibility in cold water, etc.

SUMMARY OF THE INVENTION

In accordance with the invention it has now been established that all of these disadvantages can be eliminated when fish gelatin is used in place of gelatin from warm-blooded animals.

The stable, cold water-dispersible preparations of fat-soluble substances in accordance with the invention contain fish gelatin as the protective colloid.

These preparations can be prepared in a manner known per se such as, for example, by preparing an aqueous emulsion of the active substance and a protective colloid, and if desired subsequently converting the composition into a dry powder. In the inventive process fish gelatin is used as the protective colloid.

DETAILED DESCRIPTION OF THE PREFERRED EMBODIMENTS

The term "cold water-dispersible preparations" means in the scope of the present invention liquid, as well as corresponding solid application forms. The solid application forms, i.e. preparations in pulverous form are preferred.

The term "fat-soluble substances" embraces in the scope of the present invention especially the fat-soluble vitamins A, D, E and K, carotinoids such as for example, beta-carotene, astaxanthin, apocarotenal, canthaxanthin, zeaxanthin etc. as well as poly-unsaturated fatty acids and the like. However, there will be immediately recognizable other fat-soluble substances which play a role in human or animal nutrition and, as the previously named, are usually marketed in the form of dry powders because of their water-insolubility or also their more or less pronounced stability and manipulability. Here there can be mentioned, in particular, oils and fats such as for example, sunflower oil, palm oil, beef fat and the like.

It is usually a common feature of such preparations that the active ingredients are enveloped with a protective colloid which is responsible, inter alia, for the protection of the active substance or for its stabilization, for an optimal resorption and for the water-dispersibility of the final preparation which may be required. As discussed above, the protective colloid normally used is gelatin which originates from warm-blooded animals which has certain disadvantages. In accordance with the invention it has now been established that all of these disadvantages can be eliminated when fish gelatin is used in place of gelatin from warm-blooded animals.

The stable, cold water-dispersible preparations of fat-soluble substances in accordance with the invention accordingly contain fish gelatin as the protective colloid.

These preparations can be prepared in a manner known per se such as, for example, by preparing an aqueous emulsion of the active substance and a protective colloid and if desired subsequently converting this into a dry powder. In the process in accordance with the invention fish gelatin is, however, used as the protective colloid.

The fish gelatin which is used in the scope of the present invention can be prepared in principle in a manner analogous to the gelatin of warm-blooded animals, but here fish skin is used exclusively. Moreover, skin of deep-sea fishes such as, for example, cod, shellfish, torsk etc is preferred. Such a fish gelatin has a gelling point below about 20° C., and particularly between about 5° C. and about 10° C.; this is in contrast to gelatin from warm-blooded animals which gels at about 35° C. An especially preferred fish gelatin is the gelatin obtainable under the name "Norland HiPure Liquid Gelatin" from the firm Norland Products Inc., 695 Joyce Kilmer Ave., New Brunswick, N.J., USA.

As mentioned previously, the preparations in accordance with the invention can be prepared in a manner known per se. This is normally effected by emulsifying the active substance or the active substances in a matrix with a subsequent drying of the so obtained emulsion.

In the preparation of the emulsion there can, of course, be used in addition to fish gelatin, which serves not only as an emulsifier but also as a protective colloid, additional adjuvants which are normally used in such preparations. As examples of these there can be named sugars such as, for example, saccharose, sugar alcohols, starch derivatives such as maltodextrin, milk proteins such as, for example, sodium caseinate or also vegetable proteins such as for example, soya protein, potato protein, wheat protein etc.

As a rule, all ingredients, except the active substance, are first dissolved in water, whereby the so-called matrix is obtained. Then, the active substance or the active substances are emulsified in this matrix. The preparation of the emulsion can be effected in a manner known per se, for example by vigorous stirring or also by means of ultrasonics and the like. The pressure and the temperature are not critical parameters in this procedure and the entire operation can be carried out readily at temperatures from about room temperature up to about 70° C. and under atmospheric pressure.

The ratio of oil phases (fat-soluble substances) to the accompanying substances ultimately present in the end product generally amounts from about 1%:99% to about 60% to about 40%. The precise ratios depend on the actual biological requirement with respect to active substances and on the demand for uniform and sufficiently fine distribution of the final preparations in the forms of use which are proposed for consumption. In the event that stabilizing substances are also required or desired in the preparations, then these can generally be dissolved in the oil phase. As already mentioned, the fish gelatin also serves as an emulsifier in the preparation of the emulsion. However, further emulsifiers can also be used, whereby here there comes into consideration primarily for example, ascorbyl palmitate which then, moreover, also serves as a stabilizer.

The conversion of a thus-prepared emulsion into a dry powder can also be effected in a manner known per se, for example, by normal spray-drying, by a double-dispersion process or also by a starch-catch process. In the latter process the sprayed emulsion droplets are collected in a bed of starch and subsequently dried.

The preparations in accordance with the invention can be used not only in animal nutrition but also for human nutrition. In certain instances it can also be convenient not to convert the emulsions prepared by means of fish gelatin firstly into a dry powder, but to use them directly as such.

The term "fish gelatin" in the following Examples is in each case the "Norland HiPure Gelatin" originating from the firm Norland.

The following Examples illustrate the present invention but are not intended to limit its extent in any manner. While the examples describe what are at present considered to be the preferred embodiments of this invention, it will be obvious to those skilled in the art that various changes and modifications may be made therein without departing from the invention, and it is, therefore, aimed to cover all such changes and modifications as fall within the true spirit and scope of the invention.

Unless otherwise stated, percentages and ratios relating to solvent mixtures are expressed in volume, purity data determined by gas chromatography are expressed in area %, and the remaining percentages and ratios are expressed in weight. Temperatures are in degrees Celsius (° C.), normal pressure is about 1 atmosphere, and room temperature is about 23° C. Examples were carried out as written unless otherwise indicated.

EXAMPLE 1

144 g of fish gelatin (as an about 45% aqueous solution) and 97.2 g of crystalline sugar were placed in a 600 ml glass beaker. Then, 20 ml of distilled water were added and the mixture was brought into solution while stirring with a blade stirrer (2800 r/min.) at 40° C. Thereupon, 100 g of vitamin A palmitate (1.7 million IU/g and stabilized with α-tocopherol) were emulsified in this matrix and stirred for a further 60 minutes. After this time the internal phase of the emulsion had an average particle size of about 0.6 µ. The emulsion was then diluted with 100 ml of distilled water and heated to 65° C. Then, about 1 kg of starch, fluidized by means of silicic acid, were placed in a laboratory spraying tank and cooled to about 5° C. The emulsion was then sprayed into this using a rotary spray nozzle. The thus-obtained particles, which were enveloped with starch, were then sieved off from the excess starch and dried at room temperature using compressed air. There were obtained about 330 g of dry powder having a vitamin A content of 530,000 IU/g.

EXAMPLE 2

An emulsion was prepared in an analogous manner to Example 1 starting from 117 g of fish gelatin (as an about 45% aqueous solution); 58.4 g of crystalline sugar, 20 ml of distilled water and 13.5 g of vitamin A palmitate (1.7 million IU/g, stabilized with α-tocopherol). This emulsion was diluted with 70 ml of water. The average particle diameter of the internal phase amounted to about 0.3 µ. After drying there were obtained 160 g of dry powder having a vitamin A content of 139,600 IU/g.

EXAMPLE 3

An emulsion was prepared in an analogous manner to Example 1 starting from 51.2 g of fish gelatin (as the dry substance), 76.8 g of maltodextrin MDO5 (from the firm Roquettes Freres, Lille, France), 80 ml of distilled water, 31.9 g of an oily solution of 25 g of vitamin A acetate (2.8 million IU/g) and 2.5 g of α-tocopherol in 4.4 g of arachis oil. This emulsion was diluted with 90 ml of distilled water. The average particle diameter of the internal phase amounted to 0.28 µ. After the drying operation there were obtained 195 g of dry powder having a vitamin A content of 351, 300 IU/g.

EXAMPLE 4

An emulsion was prepared in an analogous manner to Example 1 starting from 31.3 g of fish gelatin (as an about 45% aqueous solution), 42.3 g of maltodextrin MDO5 (from the firm Roquettes Freres, Lille, France), 20 ml of distilled water and 63.6 g of tocopherol acetate. This emulsion was diluted with 200 ml of water. The average particle diameter of the internal phase amounted to 0.34 µ. This emulsion was then spray-dried in a laboratory spray dryer from the firm BüSchi, Flawil, Switzerland. The inlet temperature amounted to 186° C. and the outlet temperature to 106° C. There were thus obtained 115 g of dry powder having a tocopherol acetate content of 52.1%.

EXAMPLE 5

An emulsion was prepared in an analogous manner to Example 1 starting from 28.5 g of fish gelatin (as the dry substance), 42.7 g of maltodextrin MIDOS (from the firm Roguettes Freres, Lille, France), 50 ml of distilled water and 84.8 g of an oily solution of 84 g of gamma-linolenic acid (as the triglyceride) and 0.8 g of α-tocopherol. This emulsion was diluted with 85 ml of water. The average particle diameter of the internal phase amounted to 0.4 µ. After the drying operation there were obtained 200 g of dry powder having a content of gamma-linolenic acid of 9.8%.

EXAMPLE 6 a) 18 g of fish gelatin (as the dry substance), 27 g of maltodextrin MDO5 (from the firm Roquettes Freres, Lille, France) and 14.7 g of crystalline sugar are dissolved in 180 ml of distilled water at 70° C. in a 1 L glass beaker. Then, 5 g of ascorbyl palmirate were added to the solution while stirring and the pH of the solution was adjusted to 7.5=0.2 by means of 20% sodium hydroxide solution.

b) 13 g of β-carotene, 5.5 g of arachis oil and 1.5 g of α-tocopherol were dissolved in 200 ml of chloroform in a 500 ml round flask during 15 minutes on a steam bath.

c) The β-carotene solution obtained in accordance with b) was emulsified in the solution prepared in accordance with a) in a 2 L round flask for 30 minutes at 40° C. After this time the internal phase had a particle size of about 0.18 µ. The chloroform was then removed in a short-path distillation apparatus at 50° C. under a water-jet vacuum and the emulsion was sprayed into starch in an analogous manner to Example 1. There were obtained 85 g of dry powder having a β-carotene content of 12.5%.

EXAMPLE 7

An emulsion was prepared in an analogous manner to Example 1 starting from 56.4 g of fish gelatin (as the dry substance), 84.6 g of maltodextrin MD05 (from the firm Roquettes Freres, Lille, France), 125 ml of distilled water and 159 g of sunflower oil. This emulsion was diluted with 242 ml of distilled water. The average particle diameter of the internal phase amounts to about 0.3 μ. This emulsion was then spray-dried in a transportable minor laboratory spray dryer from the firm NIRO Atomizer, S-borg, Denmark. The inlet temperature amounted to 200° C. and the outlet temperature to 90°–94° C. There were thus obtained 230 g of dry powder having an oil content of 53%.

EXAMPLE 8

An emulsion was prepared in an analogous manner to Example 1 starting from 56.4 g of fish gelatin (as the dry substance), 84.6 g of maltodextrin MS05 (from the firm Roquettes Freres, Lille, France), 125 ml of distilled water and 159 g of beef fat (stabilized with 100–200 ppm of tocopherol). This emulsion was diluted with 242 ml of distilled water. The average particle diameter of the internal phase amounted to about 0.5 μ. This emulsion was then spray-dried in a transportable minor laboratory spray drier from the firm NIRO Atomizer, S·borg, Denmark. The inlet temperature amounted to 200° C. and the outlet temperature to 90°–94° C. There were thus obtained 235 g of dry powder having a fat content of 53%.

EXAMPLE 9

An emulsion was prepared in an analogous manner to Example 1 starting from 56.4 g of fish gelatin (as the dry substance), 84.6 g of maltodextrin MD05 (from the firm Roquettes Freres, Lille, France), 125 ml of distilled water and 159 g of palm oil. This emulsion was diluted with 242 ml of distilled water. The average particle diameter of the internal phase amounted to about 0.3 μm. This emulsion was then spray-dried in a transportable minor laboratory spray drier from the firm NIRO Atomizer, S·borg, Denmark. The inlet temperature amounted to 200° C. and the outlet temperature to 90°–95° C. There were thus obtained 225 g of dry powder having an oil content of 53%.

We claim:

1. A composition comprising:
   a) a fat soluble substance; and
   b) a protective colloid of fish gelatin enveloping said fatsoluble substance to form the composition,
   said composition being stable when dispersed in cold water and said composition having a mean particle size less than or equal to about 0.6 μm in diameter.

2. The composition according to claim 1 in a pulverous form.

3. The composition according to claim 1 in a liquid form.

4. The composition according to claim 1 wherein the fat-soluble substance is a member of the group consisting of a vitamin A, a vitamin D, a vitamin E, a vitamin K, a carotinoid, and a polyunsaturated fatty acid.

5. The composition according to claim 1 wherein the fat-soluble substance comprises: an oil or a fat.

6. The composition according to claim 5 wherein the oil is sunflower oil.

7. The composition according to claim 5 wherein the oil is palm oil.

8. The composition according to claim 5 wherein the fat is beef oil.

9. The composition according to claim 1 wherein the fish gelatin is extracted from a fish skin of a deep-sea fish and has a gelling point of below about 20° C.

10. The composition according to claim 9 wherein the fish gelatin is from the deep-sea fish of the group of cod, shellfish and torsk.

11. The composition according to claim 1 wherein the composition contains a ratio of about 1% of the fat soluble solution to about 99% of the protective colloid.

* * * * *